(12) United States Patent
Fujiwara et al.

(10) Patent No.: US 12,708,319 B2
(45) Date of Patent: Aug. 18, 2026

(54) EPILEPTIC SEIZURE PREDICTING DEVICE, METHOD FOR ANALYZING ELECTROCARDIOGRAMIC INDEX DATA, SEIZURE PREDICTING COMPUTER PROGRAM, MODEL CONSTRUCTING DEVICE, MODEL CONSTRUCTING METHOD, AND MODEL CONSTRUCTING COMPUTER PROGRAM

(71) Applicant: Kyoto University, Kyoto (JP)

(72) Inventors: Koichi Fujiwara, Kyoto (JP); Fumiya Sakane, Kyoto (JP)

(73) Assignee: Kyoto University, Kyoto (JP)

( * ) Notice: Subject to any disclaimer, the term of this patent is extended or adjusted under 35 U.S.C. 154(b) by 1231 days.

(21) Appl. No.: 17/279,181

(22) PCT Filed: Aug. 27, 2019

(86) PCT No.: PCT/JP2019/033590

§ 371 (c)(1),
(2) Date: Mar. 24, 2021

(87) PCT Pub. No.: WO2020/066430

PCT Pub. Date: Apr. 2, 2020

(65) Prior Publication Data

US 2022/0000415 A1 Jan. 6, 2022

(30) Foreign Application Priority Data

Sep. 27, 2018 (JP) ................................ 2018-181414

(51) Int. Cl.
*A61B 5/0245* (2006.01)
*A61B 5/00* (2006.01)
(Continued)

(52) U.S. Cl.
CPC ............ *A61B 5/4094* (2013.01); *A61B 5/349* (2021.01); *A61B 5/352* (2021.01); *A61B 5/7203* (2013.01); *G16H 50/20* (2018.01)

(58) Field of Classification Search
CPC ..... A61B 5/4094; A61B 5/352; A61B 5/7203; A61B 5/7282; G16H 50/20
(Continued)

(56) References Cited

U.S. PATENT DOCUMENTS 4,633,884 A * 1/1987 Imai ....................... A61B 5/349 600/509
8,024,032 B1 * 9/2011 Osorio ..................... A61B 5/16 600/545
(Continued)

FOREIGN PATENT DOCUMENTS

JP 2009-519803 A 5/2009
JP 6344912 B2 6/2018

OTHER PUBLICATIONS

Notice of Reasons for Refusal in Japanese Patent Application No. 2020-548217 dated Aug. 1, 2023 (pp. 1-5) and English translation thereof (pp. 1-5).

(Continued)

*Primary Examiner* — Michael W Kahelin
*Assistant Examiner* — Karmel J Webster
(74) *Attorney, Agent, or Firm* — Jennifer L. King; Millen, White, Zelano & Branigan, P.C.; William Nixon

(57) ABSTRACT

This disclosure relates to an epileptic seizure predicting device (1) that executes a seizure predicting process (12). The seizure predicting process (12) includes: a process of providing, as input data, electrocardiographic index data generated from an electrocardiographic signal of a subject, to an autoencoder (AE) that has been provided with and has learned with, as learning input data, learning electrocardiographic index data generated from an electrocardiographic signal of an epilepsy patient, and obtaining output data which is reconstruction data of the input data; a process of calculating an error between the input data and the output data of the subject; and a detection process of detecting a sign of an epileptic seizure of the subject on the basis of whether or not the error exceeds a management limit that the error should not exceed in a case of a seizure-free interval of epilepsy.

13 Claims, 9 Drawing Sheets

(51) Int. Cl.
*A61B 5/349* (2021.01)
*A61B 5/352* (2021.01)
*G16H 50/20* (2018.01)

(58) Field of Classification Search
USPC .................................................. 600/300, 301
See application file for complete search history.

(56) References Cited

U.S. PATENT DOCUMENTS 8,068,903 B2 * 11/2011 Virag ................. A61B 5/02405 600/545
8,112,148 B2 * 2/2012 Giftakis ................. A61B 5/349 600/513
2007/0260147 A1 * 11/2007 Giftakis ............... A61N 1/3962 600/483
2008/0319281 A1 12/2008 Aarts
2010/0274303 A1 * 10/2010 Bukhman ............ A61B 5/4094 607/45
2011/0218950 A1 * 9/2011 Mirowski .............. A61B 5/372 706/58
2011/0270095 A1 * 11/2011 Bukhman .............. A61B 5/349 607/45
2012/0296175 A1 * 11/2012 Poh .................... A61B 5/02405 600/483
2013/0245462 A1 * 9/2013 Capdevila ............. G06T 7/0012 600/479
2018/0333063 A1 * 11/2018 Muchhala .............. A61B 5/243

OTHER PUBLICATIONS

International Search Report dated Nov. 12, 2019 issued in corresponding PCT/JP2019/033590 application (1 page).
Tetsuro Tatsuoka, Interface, vol. 44, No. 6 (Jun. 2018) pp. 117-125, Non-Official Translation (Research on Embedded AI Biometrics for Wearables).
Hirotsugu Hashimoto et al., “Analysis of Changes in HRV of Epileptic Patients in Preictal Period”, Japanese Society for Medical and Biological Engineering, vol. 51, (2013) p. R-198.

* cited by examiner

100
P
2
HEART RATE MEASURING INSTRUMENT
21A
21A
21A
21A
1
EPILEPTIC SEIZURE PREDICTING DEVICE
EPILEPTIC SEIZURE PREDICTION MODEL
22
51
EPILEPTIC SEIZURE PREDICTION MODEL CONSTRUCTING DEVICE
EPILEPTIC SEIZURE PREDICTION MODEL
73

(a)
I
Ith
TIME
R WAVE
R WAVE
T WAVE
P WAVE
Q WAVE
S WAVE
(b)
1
0
TIME
RRI

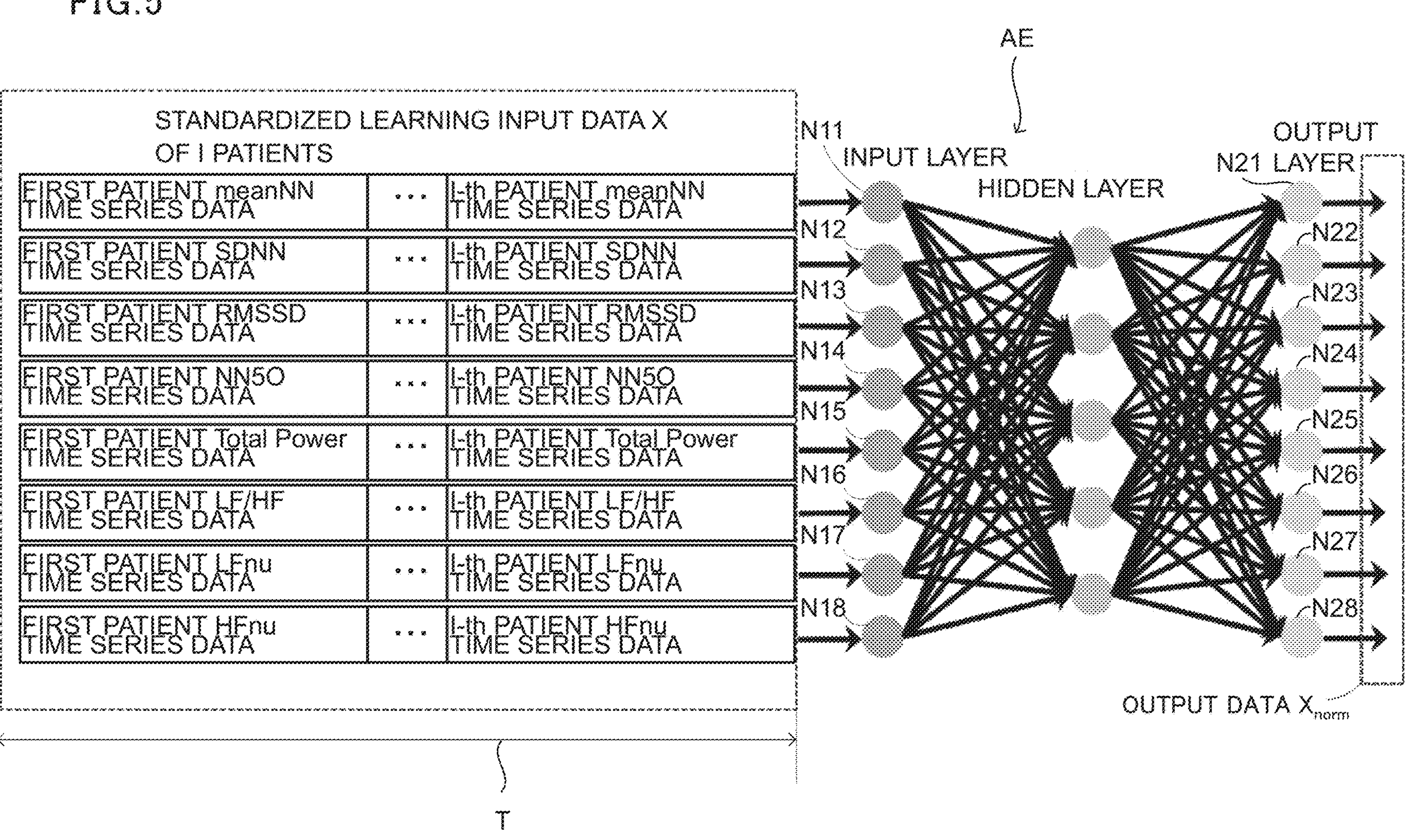

FIG.5
STANDARDIZED LEARNING INPUT DATA X OF I PATIENTS
FIRST PATIENT meanNN TIME SERIES DATA
I-th PATIENT meanNN TIME SERIES DATA
FIRST PATIENT SDNN TIME SERIES DATA
I-th PATIENT SDNN TIME SERIES DATA
FIRST PATIENT RMSSD TIME SERIES DATA
I-th PATIENT RMSSD TIME SERIES DATA
FIRST PATIENT NN5O TIME SERIES DATA
I-th PATIENT NN5O TIME SERIES DATA
FIRST PATIENT Total Power TIME SERIES DATA
I-th PATIENT Total Power TIME SERIES DATA
FIRST PATIENT LF/HF TIME SERIES DATA
I-th PATIENT LF/HF TIME SERIES DATA
FIRST PATIENT LFnu TIME SERIES DATA
I-th PATIENT LFnu TIME SERIES DATA
FIRST PATIENT HFnu TIME SERIES DATA
I-th PATIENT HFnu TIME SERIES DATA
T
N11
N12
N13
N14
N15
N16
N17
N18
INPUT LAYER
HIDDEN LAYER
AE
OUTPUT LAYER
N21
N22
N23
N24
N25
N26
N27
N28
OUTPUT DATA $X_{norm}$

FIG.8

EPILEPTIC SEIZURE PREDICTING DEVICE, METHOD FOR ANALYZING ELECTROCARDIOGRAMIC INDEX DATA, SEIZURE PREDICTING COMPUTER PROGRAM, MODEL CONSTRUCTING DEVICE, MODEL CONSTRUCTING METHOD, AND MODEL CONSTRUCTING COMPUTER PROGRAM

TECHNICAL FIELD

The present disclosure relates to an epileptic seizure predicting device, a method for analyzing electrocardiographic index data, a seizure predicting computer program, a model constructing device, a model constructing method, and a model constructing computer program.

BACKGROUND ART

To date, a device that predicts a sign of an epileptic seizure on the basis of a heart rate pattern measured with respect to a subject has been proposed (see PATENT LITERATURE 1, for example). In PATENT LITERATURE 1, a heart rate pattern known for predicting an epileptic seizure is stored, and a sign of an epileptic seizure is detected on the basis of a result of comparison between the stored heart rate pattern and a heart rate pattern obtained through measurement.

CITATION LIST

Patent Literature

PATENT LITERATURE 1: Japanese Translation of PCT International Application Publication No. 2009-519803

PATENT LITERATURE 2: Japanese Patent No. 6344912

SUMMARY OF INVENTION

However, in actuality, no heart rate pattern that predicts an epileptic seizure is known. In the technology described in the PATENT LITERATURE, data that indicates a heart rate pattern that predicts an epileptic seizure is essential. In addition, the frequency of occurrence of an epileptic seizure during measurement of data of heart rates of a subject is low, and the truth is that it is difficult to obtain a heart rate pattern (heart rate pattern that indicates a sign of an epileptic seizure) that predicts an epileptic seizure.

Here, PATENT LITERATURE 2 discloses discerning a sign of an epileptic seizure based on a seizure sign detection model. A seizure sign detection model of PATENT LITERATURE 2 is generated by performing main component analysis on a plurality of pieces of second index data that indicate index values for a plurality of respective types of indexes related to the heart rate.

The seizure sign detection model according to PATENT LITERATURE 2 is generated on the basis of sample data generated from an electrocardiographic signal in a seizure-free interval, and does not require data indicating a sign of an epileptic seizure. The present inventors which includes one of the inventors of PATENT LITERATURE 2 have found a new method that allows data indicating a sign of an epileptic seizure to be nonessential, due to an approach different from that of the method disclosed in PATENT LITERATURE 2.

A mode of the present disclosure is an epileptic seizure predicting device configured to execute a seizure predicting process. The seizure predicting process includes: a process of providing, as input data, electrocardiographic index data generated from an electrocardiographic signal of a subject, to an autoencoder that has been provided with and has learned with, as learning input data, learning electrocardiographic index data generated from an electrocardiographic signal of an epilepsy patient, and obtaining output data which is reconstruction data of the input data; a process of calculating an error between the input data and the output data of the subject; and a detection process of detecting a sign of an epileptic seizure of the subject on the basis of whether or not the error exceeds a management limit that the error should not exceed in a case of a seizure-free interval of epilepsy.

Another mode of the present disclosure is a method to be performed by a computer in order to analyze electrocardiographic index data generated from an electrocardiographic signal of a subject.

Another mode of the present disclosure is a computer program configured to cause a computer to execute a seizure predicting process.

Another mode of the present disclosure is a model constructing device configured to execute a model constructing process for epileptic seizure prediction. The model constructing process includes: a process of providing, as input data, electrocardiographic index data generated from an electrocardiographic signal of a subject, to an autoencoder that has been provided with and has learned with, as learning input data, learning electrocardiographic index data generated from an electrocardiographic signal of an epilepsy patient, and obtaining output data which is reconstruction data of the input data; a calculation process of calculating an error between the input data and the output data; and a setting process of setting, on the basis of the error, a management limit that the error should not exceed when the subject is in a seizure-free interval of epilepsy.

Another mode of the present disclosure is a method for constructing a model for epileptic seizure prediction.

Another mode of the present disclosure is a computer program configured to cause a computer to execute a model constructing process.

Further details will be described as an embodiment described later.

BRIEF DESCRIPTION OF DRAWINGS

FIG. 2(*b*) shows R wave data.

FIG. 5 illustrates an autoencoder.

FIG. 8 is a flow chart of a seizure predicting process.

DESCRIPTION OF EMBODIMENTS

Figure 1:
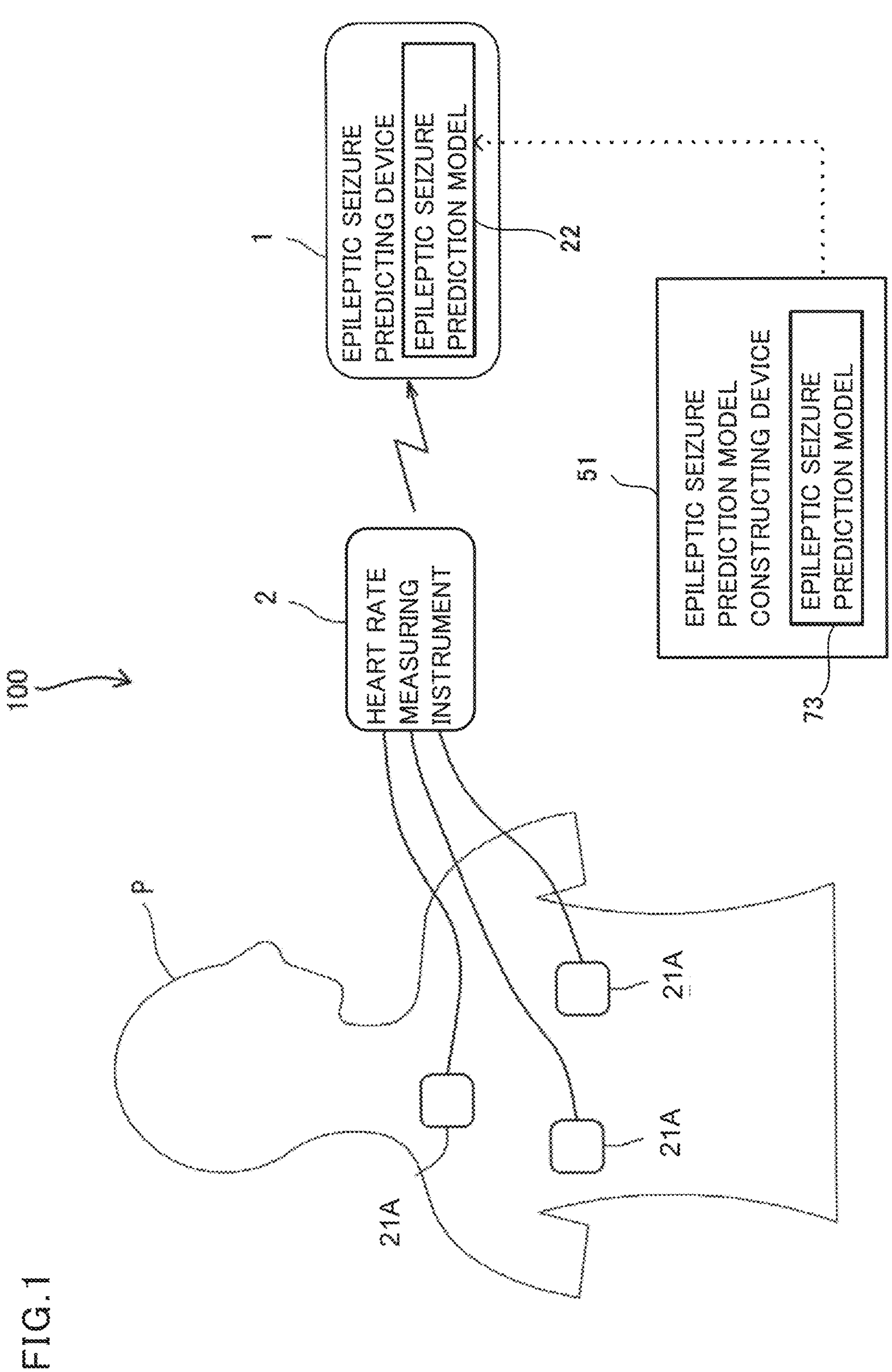
FIG. 1 is a configuration diagram of a system 100 including an epileptic seizure predicting device.

1. Outlines of Epileptic Seizure Predicting Device, Method for Analyzing Electrocardiographic Index Data, Seizure Predicting Computer Program, Model Constructing Device, Model Constructing Method, Model Constructing Computer Program (1) An epileptic seizure predicting device according to an embodiment executes a seizure predicting process. In the seizure predicting process, an autoencoder is used. The autoencoder is a neural network that is caused to learn to reconstruct, from learning data serving as input data, data that is equal to the input data (the learning data), and to output the resultant data as reconstruction data. In the embodiment, the autoencoder has been provided with and has learned with, as learning input data, learning electrocardiographic index data generated from an electrocardiographic signal of an epilepsy patient. The number of epilepsy patients is one or a plurality. The learning electrocardiographic index data need not include data indicating a sign of an epileptic seizure, and only has to be data in a seizure-free interval. Therefore, the learning electrocardiographic index data can be easily obtained.

Since the frequency of occurrence of an epileptic seizure is low, the learning electrocardiographic index data generated from an electrocardiographic signal of an epilepsy patient is, inevitably, data that is in a seizure-free interval only or data that is mainly in a seizure-free interval. In the autoencoder having learned using such data, output data can be accurately reconstructed from the input data in the seizure-free interval. Meanwhile, when a sign of an epileptic seizure appears, an error (reconstruction error) between the input data and the output data becomes large. Using this, the seizure predicting process of the embodiment includes a process of providing the autoencoder with, as input data, electrocardiographic index data generated from an electrocardiographic signal of a subject, and obtaining output data which is reconstruction data of the input data. The seizure predicting process further includes a process of calculating an error between the input data and the output data of the subject, and a detection process of detecting a sign of an epileptic seizure of the subject on the basis of whether or not the error exceeds a management limit that the error should not exceed in a case of a seizure-free interval of epilepsy. According to these processes, when the error between the input data and the output data of the subject becomes large to exceed the management limit, a sign of an epileptic seizure can be detected.

According to the seizure predicting process of the embodiment, even when data indicating a sign of an epileptic seizure is made nonessential, a sign of an epileptic seizure can be detected.

The autoencoder may be included in the epileptic seizure predicting device or may be included in a device (e.g., a server computer on the Internet) other than the epileptic seizure predicting device. In this case, the epileptic seizure predicting device and the device (such as a server computer) functioning as the autoencoder are communicably connected with each other via a network. The epileptic seizure predicting device provides input data via the network to the autoencoder. The epileptic seizure predicting device obtains output data via the network from the autoencoder. That is, in the seizure predicting process, the process of obtaining the output data may be a process of providing via a network, as input data, electrocardiographic index data generated from an electrocardiographic signal of a subject, to the autoencoder that has been provided with and has learned with, as learning input data, learning electrocardiographic index data generated from an electrocardiographic signal of an epilepsy patient, and obtaining output data which is reconstruction data of the input data, via the network from the autoencoder.

(2) Preferably, the learning electrocardiographic index data is generated from an electrocardiographic signal in a seizure-free interval of the epilepsy patient. In this case, data indicating a sign of an epileptic seizure is not required, which is advantageous. In addition, the electrocardiographic index data of the subject also only has to be generated from an electrocardiographic signal in a seizure-free interval of the subject.

(3) Preferably, in the detection process, the sign of the epileptic seizure of the subject is detected when the error continuously exceeds the management limit for a predetermined time. In this case, erroneous detection due to momentary increase of the error can be inhibited.

(4) Preferably, the electrocardiographic index data is calculated on the basis of an RRI (R-R Interval) generated from the electrocardiographic signal of the subject.

(5) Preferably, the learning electrocardiographic index data is generated from electrocardiographic signals of a plurality of epilepsy patients. In addition, preferably, the plurality of epilepsy patients include the subject and an epilepsy patient other than the subject.

(6) The epileptic seizure predicting device may be configured to further execute an adjusting process for adjusting the management limit stored in advance in a storage device. In this case, a doctor or a user can adjust the management limit in accordance with the subject.

(7) A method for analyzing electrocardiographic index data according to the embodiment is a method performed by a computer in order to analyze electrocardiographic index data generated from an electrocardiographic signal of a subject. The method includes the steps, performed by the computer, of: providing, as input data, electrocardiographic index data generated from an electrocardiographic signal of the subject, to an autoencoder that has been provided with and has learned with, as learning input data, learning electrocardiographic index data generated from an electrocardiographic signal of an epilepsy patient, and obtaining output data which is reconstruction data of the input data; calculating an error between the input data and the output data of the subject; and determining whether or not the error exceeds a management limit that the error should not exceed in a case of a seizure-free interval of epilepsy.

(8) A seizure predicting computer program according to the embodiment is a computer program configured to cause a computer to execute a seizure predicting process. The seizure predicting process includes: a process of providing, as input data, electrocardiographic index data generated from an electrocardiographic signal of a subject, to an autoencoder that has been provided with and has learned with, as learning input data, learning electrocardiographic index data generated from an electrocardiographic signal of an epilepsy patient, and obtaining output data which is reconstruction data of the input data; a process of calculating an error between the input data and the output data of the subject; and a detection process of detecting a sign of an epileptic seizure of the subject on the basis of whether or not the error exceeds a management limit that the error should not exceed in a case of a seizure-free interval of epilepsy. The computer program is stored in a computer-readable storage medium.

(9) A model constructing device according to the embodiment executes a model constructing process for epileptic seizure prediction. The model constructing process includes: a process of providing, as input data, electrocardiographic index data generated from an electrocardiographic signal of a subject, to an autoencoder that has been provided with and has learned with, as learning input data, learning electrocardiographic index data generated from an electrocardiographic signal of an epilepsy patient, and obtaining output data which is reconstruction data of the input data; a calculation process of calculating an error between the input data and the output data; and a setting process of setting, on the basis of the error, a management limit that the error should not exceed when the subject is in a seizure-free interval of epilepsy.

(10) Preferably, in the setting process, the management limit is set such that: a predetermined proportion of errors that accounts for a majority of a plurality of the errors calculated in the calculation process does not exceed the management limit; and a remainder of the plurality of the errors exceeds the management limit. When the learning electrocardiographic index data is generated from an electrocardiographic signal in a seizure-free interval of the epilepsy patient, the calculated plurality of errors are all errors that occur in a seizure-free interval. When the management limit is to set such that all of the plurality of errors fall in a seizure-free interval, it is difficult to appropriately set the management limit. In contrast, in the embodiment, the setting only has to be performed such that: a predetermined proportion of errors that accounts for a majority of the plurality of the errors does not exceed the management limit; and a remainder of the plurality of the errors exceeds the management limit. Thus, the management limit can be easily set.

(11) Preferably, for example, the predetermined proportion that accounts for the majority is a proportion in a range of not less than 90% and less than 100%. The lower limit of the predetermined proportion is more preferably not less than 95%, and further preferably not less than 98%.

(12) A model constructing method according to the embodiment is a method for constructing a model for epileptic seizure prediction. The method includes: providing, as input data, electrocardiographic index data generated from an electrocardiographic signal of a subject, to an autoencoder that has been provided with and has learned with, as learning input data, learning electrocardiographic index data generated from an electrocardiographic signal of an epilepsy patient, and obtaining output data which is reconstruction data of the input data; calculating an error between the input data and the output data; and setting, on the basis of the error, a management limit that the error should not exceed when the subject is in a seizure-free interval of epilepsy.

(13) A model constructing computer program according to the embodiment causes a computer to execute a model constructing process. The model constructing process includes: a process of providing, as input data, electrocardiographic index data generated from an electrocardiographic signal of a subject, to an autoencoder that has been provided with and has learned with, as learning input data, learning electrocardiographic index data generated from an electrocardiographic signal of an epilepsy patient, and obtaining output data which is reconstruction data of the input data; a calculation process of calculating an error between the input data and the output data; and a setting process of setting, on the basis of the error, a management limit that the error should not exceed when the subject is in a seizure-free interval of epilepsy.

<2. Examples of Epileptic Seizure Predicting Device, Method for Analyzing Electrocardiographic Index Data, Seizure Predicting Computer Program, Model Constructing Device, Model Constructing Method, Model Constructing Computer Program>

FIG. 1 is a schematic diagram showing a configuration of a system 100 including an epileptic seizure predicting device 1 according to an embodiment. The system 100 includes the epileptic seizure predicting device 1 (hereinafter, referred to as a "predicting device 1"); and a heart rate measuring instrument 2. The predicting device 1 and the heart rate measuring instrument 2 are communicable with each other. The communication may be wireless communication or wired communication.

The heart rate measuring instrument 2 is a small, light-weight wearable terminal that is attached to the body of a subject P and that is for measuring the heart rate of the subject P. The heart rate measuring instrument 2 has connected thereto a plurality of (three in FIG. 1) electrodes 21A that are attached to the surface of the body of the subject P. The three electrodes 21A are, for example, a positive electrode, a negative electrode, and a ground electrode. An example of the wearable terminal functioning as the heart rate measuring instrument 2 is a smartwatch that has a heart rate measuring function. The wearable terminal itself may function as the predicting device 1 and the heart rate measuring instrument 2.

Figure 2:
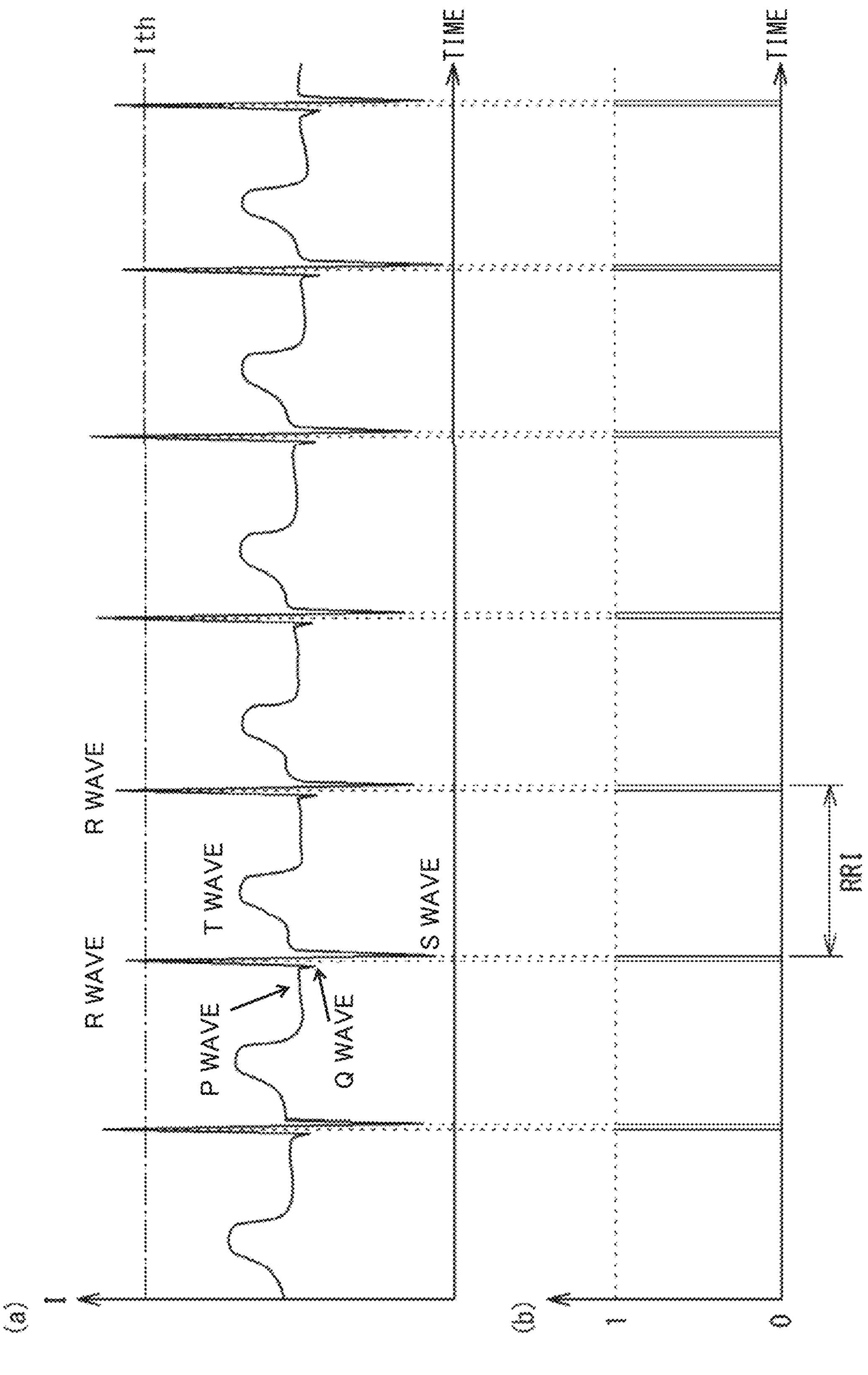
FIG. 2(*a*) shows an example of an electrocardiographic signal.

FIG. 2(*a*) shows an example of an electrocardiographic signal. In FIG. 2(*a*), the vertical axis represents electric potential, and the horizontal axis represents time. When a heart rate is measured by using the electrodes 21A, electric potential variation in the form of P to T waves as shown in FIG. 2(*a*) appears cyclically. A peak that has a highest electric potential in the electric potential variation in a unit cycle is referred to as an R wave, and the heart beats at the timing of the R wave. The heart rate measuring instrument 2 transmits R wave data representing the R wave, to the predicting device 1.

FIG. 2(*b*) shows R wave data corresponding to the electrocardiographic signal in FIG. 2(*a*). As shown in FIG. 2(*b*), the R wave data is data that represents a rectangular pulse train in which "1" is set for each period (a period in which a signal intensity I exceeds a predetermined intensity threshold Ith) that corresponds to the R wave in the electrocardiographic signal, and "0" is set for the other periods. The interval between R waves is referred to as an RRI (R-R Interval).

Figure 3:
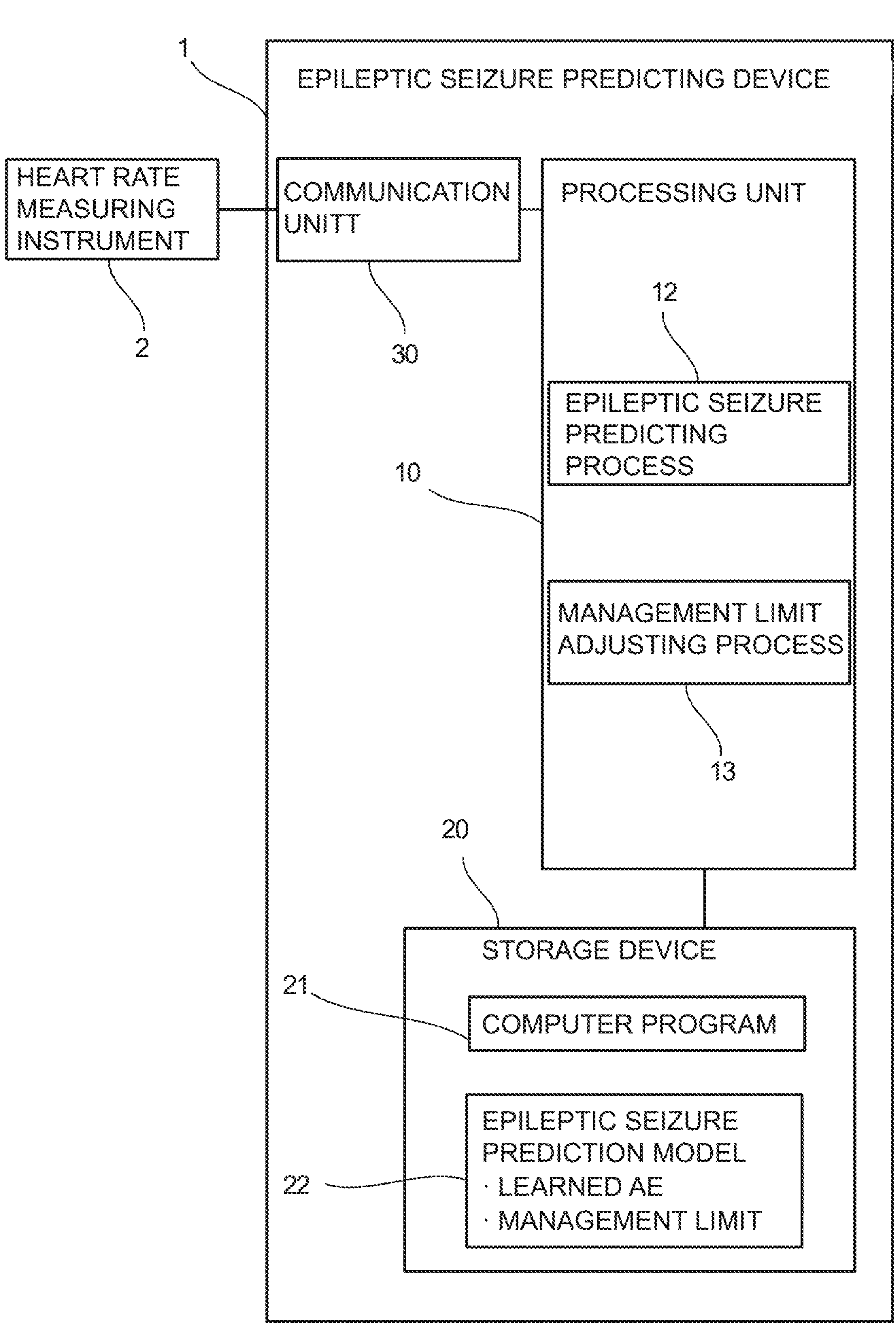
FIG. 3 is a configuration diagram of the epileptic seizure predicting device.

The predicting device 1 receives the R wave data transmitted from the heart rate measuring instrument 2, and detects a sign of an epileptic seizure of the subject P, thereby predicting an epileptic seizure. As shown in FIG. 3, the predicting device 1 is implemented as a computer including a processing unit 10 and a storage device 20. The processing unit 10 is a CPU, for example. The predicting device 1 also includes a communication unit 30 for communication with the heart rate measuring instrument 2. The communication unit 30 may be a communication mechanism for short-range wireless communication such as Bluetooth (registered trademark), or may be a communication mechanism for wireless LAN.

Preferably, the computer implementing the predicting device 1 is a mobile terminal, such as a smartphone or a tablet, for example. This is preferable because the mobile terminal held by the subject P can be utilized as the predicting device 1. If a mobile terminal is used, also when a detected presage of an epileptic seizure is to be notified of to the subject P, notification functions (outputting function of sound, light, or characters) of the mobile terminal can be utilized, which is preferable. The mobile terminal may be a wearable device such as a smartwatch. The predicting device 1 may be implemented by a plurality of computers. For example, the predicting device 1 may be implemented as a combination of a plurality of mobile terminals. An example of the plurality of mobile terminals is a smartphone and a smartwatch.

The computer implementing the predicting device 1 may be a server computer on a network such as the Internet. In this case, the R wave data transmitted from the heart rate measuring instrument 2 of the subject P is transmitted to the server computer via a network such as the Internet. When the server computer has detected a presage of an epileptic seizure, the server computer may notify, via the network, a terminal (mobile terminal, etc.) of the subject P.

The storage device 20 of the predicting device 1 has stored therein a computer program 21 for causing the processing unit 10 to execute an epileptic seizure predicting process 12. As a result of the processing unit 10 executing the computer program 21, the computer functions as the predicting device 1. The computer program 21 also causes the processing unit 10 to execute a management limit adjusting process 13 described later.

The storage device 20 of the predicting device 1 has stored therein data for forming an epileptic seizure prediction model 22 to be used in the epileptic seizure predicting process 12. In the embodiment, data for forming the seizure prediction model 22 includes parameters for causing a processing unit 60 to function as a learned autoencoder AE. The parameters for causing the processing unit 60 to function as an autoencoder AE are parameters in a neural network and include a weight between units in the neural network, a bias of each unit, an activation function, and the like. The parameters such as the weight and the like have been optimized through learning. The model 22 of the embodiment also includes a management limit L. The management limit L will be described later.

The predicting device 1 itself may not necessarily include the autoencoder AE, and an external device communicable with the predicting device 1 may include the autoencoder AE. For example, a case in which the computer program 21 downloaded via the Internet from a computer program providing server is installed to a mobile terminal held by the subject P, whereby the predicting device 1 is constructed, is assumed. In this case, the downloaded computer program 21 need not include data (parameters) for causing the mobile terminal held by the subject P to function as the autoencoder AE. The autoencoder AE may be an autoencoder AE constructed on a server computer on a network such as the Internet. In a case where the scale of the autoencoder AE increases, a calculation load increases, which may result in an insufficient throughput on the terminal held by the subject P. In contrast, if an external device such as a server computer is used, a high throughput necessary for execution of the autoencoder AE can be easily assured.

Figure 4:
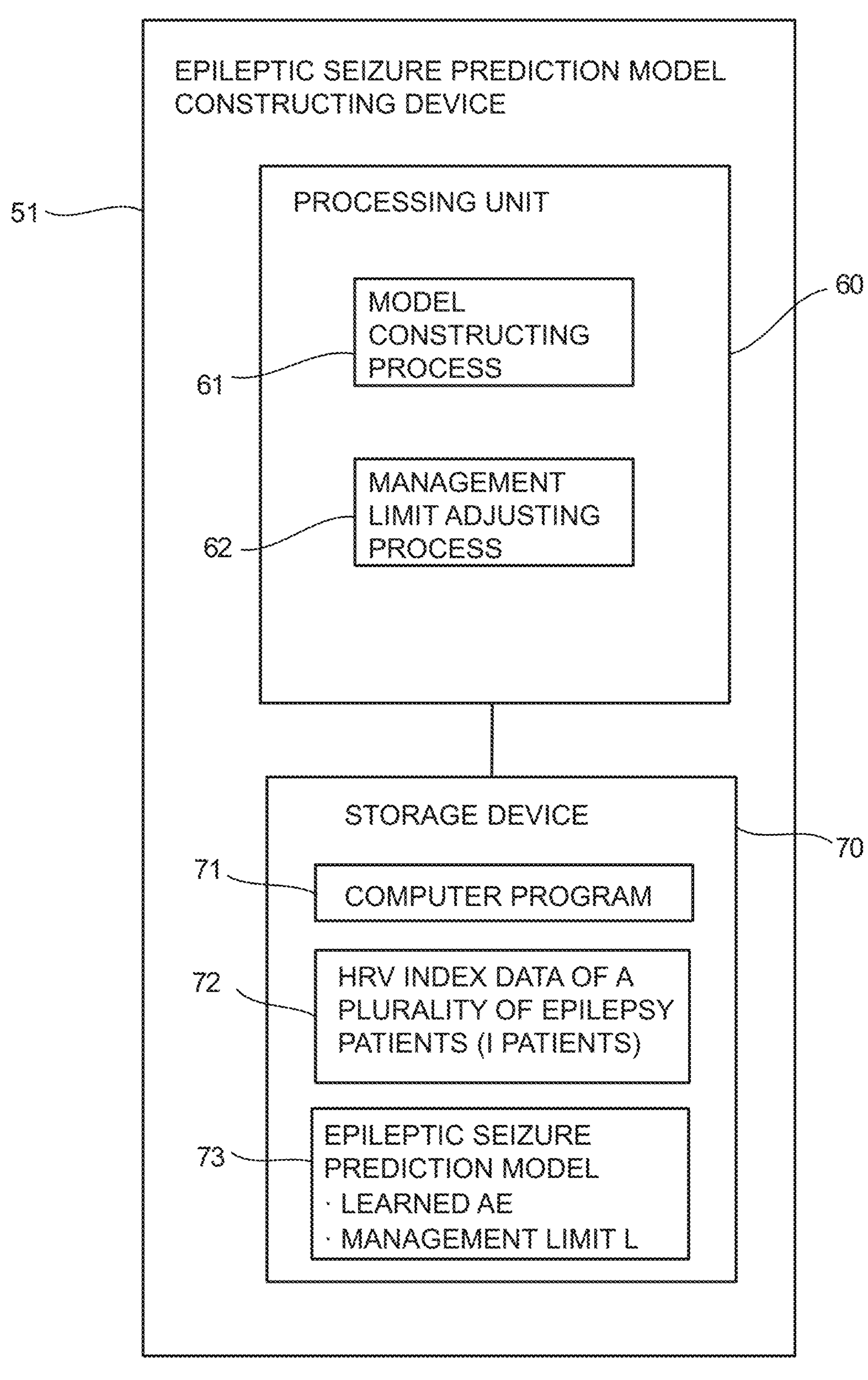
FIG. 4 is a configuration diagram of an epileptic seizure prediction model constructing device.

FIG. 4 shows an epileptic seizure prediction model constructing device 51 (hereinafter, referred to as a "constructing device 51"). The constructing device 51 executes a model constructing process 61 for epileptic seizure prediction. Data forming an epileptic seizure prediction model 73 constructed through the model constructing process 61 is stored in the storage device 20 of the predicting device 1, and functions as a prediction model 22 in the predicting device 1.

The constructing device 51 is implemented as a computer including the processing unit 60 and a storage device 70. The processing unit 60 is a CPU, for example. The constructing device 51 is, for example, a server computer on a network such as the Internet. The storage device 70 of the constructing device 51 has stored therein a computer program 71 for causing the processing unit 60 to execute the model constructing process 61. As a result of the processing unit 60 executing the computer program 71, the computer functions as the constructing device 51. The computer program 71 can also cause the processing unit 60 to execute a management limit adjusting process 62 described later.

The constructing device 51 and the predicting device 1 may be implemented by the same computer (e.g., a server computer on a network). However, it is preferable that the constructing device 51 and the predicting device 1 are implemented by different computers. In the latter case (e.g., when the constructing device 51 is a server computer and the predicting device 1 is a mobile terminal), data forming a seizure prediction model is transmitted from the constructing device 51 to the predicting device 1. The data forming the seizure prediction model may be stored once from the constructing device 51 into a data transmission server, and then, transmitted from the data transmission server to the predicting device 1. The constructing device 51 may function as an autoencoder AE to be used by the predicting device 1.

In the model constructing process 61 of the constructing device 51, first, learning by an autoencoder AE to be used in epileptic seizure prediction is performed. The autoencoder AE shown in FIG. 5 includes an input layer, a hidden layer, and an output layer. The autoencoder AE shown in FIG. 5 includes, as an example, eight units of N11, N12, N13, N14, N15, N16, N17, and N18 in the input layer, and eight units of N21, N22, N23, N24, N25, N26, N27, and N28 in the output layer. That is, the number of input variables and the number of output variables of the autoencoder AE in FIG. 5 are each eight. In FIG. 5, the number of the hidden layers is one, but the number of the hidden layers is not limited to one, and can be determined as appropriate.

As a transfer function for an encoder of an autoencoder, a logistic sigmoid transfer function, a positive saturating linear transfer function, a normalization linear unit, or a hyperbolic tangent sigmoid transfer function can be adopted, for example. As a transfer function for a decoder, a linear transfer function can be adopted, for example. According to an experiment performed by the present inventors, in epileptic seizure prediction according to the embodiment, a logistic sigmoid transfer function is preferable as the transfer function for the encoder.

In the embodiment, eight variables provided to the autoencoder AE as learning input data are eight indexes (HRV indexes) regarding heart rate variability (HRV). In the embodiment, the following are adopted as the eight HRV indexes.

1) meanNN: Mean value of RRI
2) SDNN: Standard deviation of RRI
3) RMSSD: Root mean square value of the difference between adjacent RRIs
4) NN50: The number of times the difference between adjacent RRIs exceeds 50 ms
5) Total Power: Variance of RRI
6) LF/HF: Ratio of LF to HF
7) LFnu: LF/Total Power
8) HFnu: HF/Total Power HF refers to power at a high frequency (0.15 to 0.40 Hz) with respect to power spectrum density (PSD) of time series data of RRI. LF refers to power at a low frequency (0.04 to 0.15 Hz) with respect to the PSD.

Among the eight HRV indexes above, 1) to 5) are each a time domain index, and 6) to 8) are each a frequency domain index. The time domain index is calculated directly from the time series data of RRI (RRI data). The frequency domain index is calculated from the PSD of the RRI data. The RRI data is not sampled at equal intervals, and thus, in order to obtain PSD, sampling needs to be performed. The PSD is calculated from re-sampled RRI data by using an auto regression (AR) model or a Fourier transform.

The storage device 70 of the constructing device 51 has stored therein HRV index data 72 which is electrocardiographic index data of a plurality of (I patients: I is an integer of 2 or greater) epilepsy patients. The HRV index data 72 of each patient i (i is an integer from 1 to I) includes the eight HRV indexes described above. Since the eight HRV indexes are each time series data, HRV index data of each patient i (i is an integer from 1 to I) is a set of eight pieces of time series data.

In the embodiment, the HRV index data 72 is generated from an electrocardiographic signal in a seizure-free interval of each of a plurality of epilepsy patients. The electrocardiographic signal in the seizure-free interval can be easily obtained, which is suitable. When an electrocardiographic signal that indicates a sign of an epileptic seizure can be obtained, the HRV index data 72 may be generated from the electrocardiographic signal that indicates a sign of an epileptic seizure and an electrocardiographic signal in a seizure-free interval.

The HRV index data 72 of a plurality of (I patients) epilepsy patients to be used in learning by an autoencoder AE may or may not include HRV index data of the subject who is the user of the predicting device 1. When the data 72 of the plurality of epilepsy patients includes data of the subject, more appropriate learning in which characteristics of the subject are reflected can be performed.

For learning by the autoencoder AE, the eight pieces of HRV index time series data included in the HRV index data 72 of a plurality of epilepsy patients are standardized to be provided, as learning electrocardiographic index data, to the input layer of the autoencoder AE. For example, meanNN time series data of a plurality of epilepsy patients is provided to the unit N11. Thereafter, similarly, SDNN time series data is provided to the unit N12, RMSSD time series data is provided to the unit N13, NN50 time series data is provided to the unit N14, Total Power time series data is provided to the unit N15, LF/HF time series data is provided to the unit N16, LFnu time series data is provided to the unit N17, and HFnu time series data is provided to N18. The method for providing the autoencoder AE with the HRV index data 72 as learning electrocardiographic index data is similar to a method for providing the autoencoder AE with the HRV index data 72 in order to set the management limit L when performing the model constructing process 61 described later. Details will be described later.

In the autoencoder AE, learning is performed such that: input data inputted to the input layer of the autoencoder AE is subjected to dimensionality reduction in the hidden layer; and data equal to the input data is reconstructed, to be outputted from the output layer. Therefore, in the learned autoencoder AE, output data obtained by reconstructing the inputted meanNN is outputted from the unit N21 of the output layer. Similarly, output data obtained by reconstructing SDNN is outputted from the unit N22, output data obtained by reconstructing RMSSD is outputted from the unit N23, output data obtained by reconstructing NN50 is outputted from the unit N24, output data obtained by reconstructing Total Power is outputted from the unit N25, output data obtained by reconstructing LF/HF is outputted from the unit N26, output data obtained by reconstructing LFnu is outputted from the unit N27, and output data obtained by reconstructing HFnu is outputted from the unit N28. The number of learning epochs is not limited in particular, but can be set to about 200 times to 3000 times, for example.

Parameters of the learned autoencoder AE are stored into the storage device 70 as a part of data for forming the seizure prediction model 73.

Figure 6:
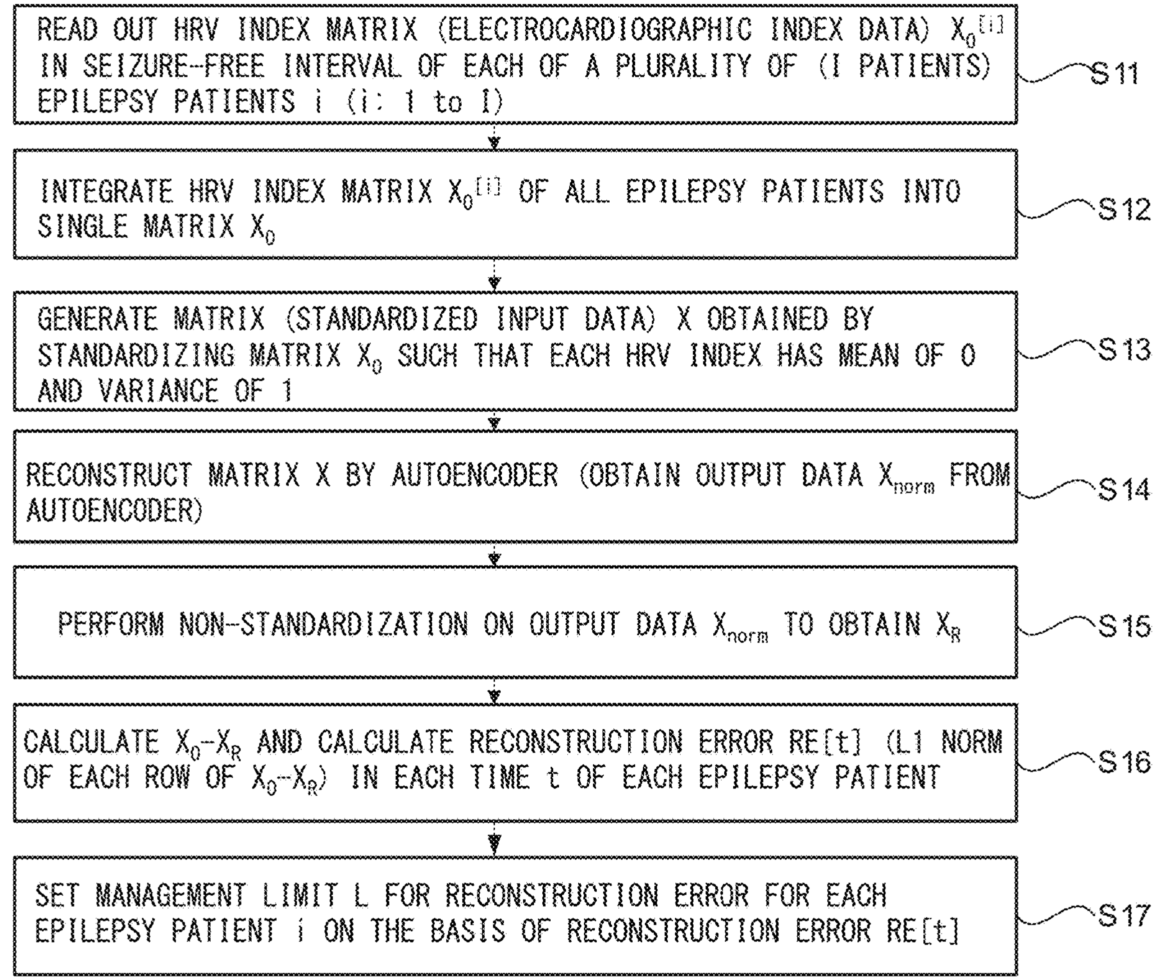
FIG. 6 is a flow chart of a model constructing process.

Subsequently, the management limit L is set by using the learned autoencoder AE. FIG. 6 shows a procedure for setting the management limit L in the model constructing process 61. First, in step S11, the processing unit 60 reads out, from the storage device 70, HRV index data (electrocardiographic index data) 72 of each of a plurality of (I patients) epilepsy patients i. The read out HRV index data 72 serves as input data to the autoencoder AE. In the following, HRV index data 72 of each patient i will be handled as an HRV index matrix $X_0^{[i]}$. The HRV index matrix $X_0^{[1]}$ has eight pieces of HRV index time series data for a patient i, as elements of the matrix.

Subsequently, in step S12, HRV index matrices $X_0^{[1]}$ of all of the plurality of epilepsy patients i are integrated into a single matrix $X_0$. Then, in step S13, the matrix $X_0$ is standardized such that each HRV index has a mean of 0 and a variance of 1 (generation of matrix X that serves as standardized input data). FIG. 5 shows standardized input data X obtained through integration of corresponding data of the plurality of patients. The integration of the data of the plurality of (I patients) patients is obtained as follows: time series data of the first epilepsy patient (the first patient) is connected to, at the end thereof, time series data of the second epilepsy patient (the second patient), and thereafter, in a similar manner, connected up to the I-th epilepsy patient (the I-th patient), whereby time series data of I patients are connected together.

When the time length of HRV index time series data of each patient i is defined as Ti[s], a time length T of each HRV index time series data in the integrated standardized input data is $T=\Sigma_{i=1}^{I}(Ti)[s]$. As for the standardized input data, a value corresponding to each discrete time t (t is a value from 0 to T) is sequentially provided to the autoencoder AE. Here, it is assumed that, in the standardized input data represented as the matrix X, eight elements included in the same row of the matrix X indicate values of the eight HRV indexes corresponding to the same time t (of the same person).

When values of the eight HRV indexes corresponding to a time t are provided as input data to the autoencoder AE, the autoencoder AE reconstructs the values of the eight HRV indexes corresponding to the time t, and outputs the obtained values as output data. Therefore, when the standardized input data (matrix X) corresponding to the entire time length T is provided to the autoencoder AE, the autoencoder AE outputs output data corresponding to the time length T, i.e., a matrix $X_{norm}$ having the same matrix size of the matrix X, as the output data (step S14).

The processing unit 60 subjects the output data $X_{norm}$ to non-standardization, to obtain a non-standardized output data $X_R$ (step S15). Non-standardization is a process inverse to standardization performed in step S13.

Subsequently, the processing unit 60 calculates $X_0$-$X_R$, and calculates a reconstruction error RE(t) in each time t of each epilepsy patient i (step S16). The reconstruction error RE(t) is an error between input data and output data in the time t.

Although the error between the input data and the output data is calculated for each HRV index, the reconstruction error RE(t) is, in the embodiment, calculated as an L1 norm of each row of $X_0$-$X_R$. Each row of $X_0$-$X_R$ indicates (reconstruction error of meanNN, reconstruction error of SDNN, reconstruction error of RMSSD, reconstruction error of NN50, reconstruction error of Total Power, reconstruction error of LF/HF, reconstruction error of LFnu, reconstruction error of HFnu), in the time t corresponding to the row. When a row (corresponding to the time t) in $X_0$-$X_R$ is (−1, −2, −3, −4, 4, 3, 2, 1), for example, the L1 norm is 20. Therefore, the reconstruction error RE(t) in the time t is 20.

In the matrix $X_0$-$X_R$, the row corresponding to the patient i is known from the operation of the integration (step S12). Thus, through calculation of the L1 norm in each row, a reconstruction error RE(t) in each time t of each epilepsy patient i can be obtained. That is, in step S16, time series data of a reconstruction error RE(t) of each epilepsy patient i is obtained. The reconstruction error RE(t) time series data of the patient i is formed having a plurality of discrete errors in the time Ti, which is the data time width.

As described above, in the embodiment, the management limit L is not set for each of a plurality of HRV indexes. Instead, a single management limit L is set from errors of a plurality of HRV indexes (difference between input data and output data). Although the management limit L may be set for each of a plurality of HRV indexes, the experiment by the present inventors revealed the following. That is, in the epileptic seizure prediction of the embodiment, a better seizure prediction accuracy was obtained when a single management limit L is set from errors of a plurality of HRV indexes than when a management limit L is set for each of a plurality of HRV indexes and then a seizure sign is predicted if the number of HRV indexes exceeding management limits has become equal to or greater than a predetermined number.

Figure 7:
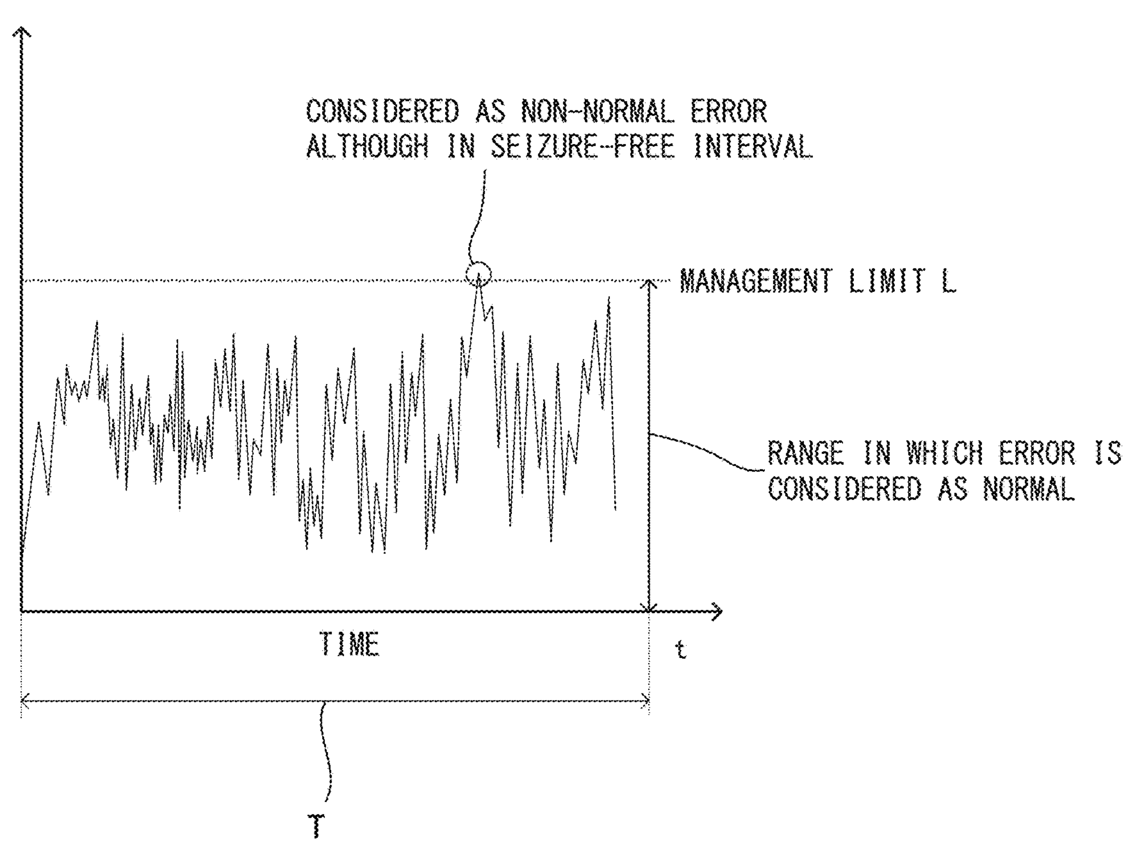
FIG. 7 illustrates setting of a management limit.

FIG. 7 shows a schematic diagram of time series data of reconstruction error RE(t). On the basis of the time series data of this reconstruction error RE(t), the processing unit 60 sets a management limit L for the reconstruction error for each epilepsy patient i (step S17). The management limit L is an index for determining that the HRV indexes of the patient i is normal. When the reconstruction error RE(t) does not exceed the management limit L, i.e., is equal to or lower than the management limit L, it is determined that the HRV indexes are normal. Here, being normal refers to the patient i being in a seizure-free interval. In the embodiment, a sign of an epileptic seizure of the patient i is detected on the basis of a reconstruction error RE(t) exceeding the management limit L.

The management limit L is set such that: with respect to a certain patient i, a predetermined proportion of errors that accounts for a majority of a plurality of errors included in reconstruction error RE(t) time series data does not exceed the management limit L; but the remainder other than the predetermined proportion exceeds the management limit L. Here, the predetermined proportion is 99%. That is, the management limit L is set such that 99% of the plurality of errors included in the time series data is determined to be normal. In FIG. 7, a very small part (corresponding to 1%) of the reconstruction error RE(t) included in the time series data exceeds the management limit L. In a case where the HRV index data 72 provided to the autoencoder AE has been generated from an electrocardiographic signal in a seizure-free interval of the patient i, the HRV index, at a time point t, that exceeds the management limit L should originally be regarded as normal. However, in the embodiment, the error at this time point t is regarded as not being normal.

If the management limit L is to be set such that all of the plurality of errors included in the time series data are regarded as normal, the management limit L should be set higher than the management limit L shown in FIG. 7. However, there is no guideline that indicates how much higher the management limit L should be set. Therefore, it is difficult to appropriately set the management limit L. In contrast, in the present embodiment, a clear and unified management limit L can be easily set.

The above-described setting of the management limit L is performed for each patient i, and the management limit L for each patient i is stored, into the storage device 70, as a part of data forming the epileptic seizure prediction model 73. In the embodiment, the epileptic seizure prediction model 73 of the patient i is composed of the learned autoencoder AE and the management limit L of the patient i.

The processing unit 60 can execute the management limit adjusting process 62 (see FIG. 4) for adjusting (changing) the management limit L set as described above. For example, the management limit adjusting process 62 is a process that allows a specialist such as a doctor to refer to a set management limit L via a network and perform an operation of slightly adjusting the set management limit (default value) L to a value appropriate for an individual patient i. For example, the management limit adjusting process 62 includes: a process of causing a terminal used by a specialist such as a doctor to output a set management limit (default value) L; and a process of receiving, from the terminal used by the specialist such as a doctor, an operation of adjusting the set management limit (default value) L, and storing the adjusted management limit L into the storage device 70.

The management limit adjusting process 62 may also be used for setting a management limit L for an epilepsy patient j other than the plurality of epilepsy patients (I patients) used in the procedure shown in FIG. 6. For example, a mean value of management limits L of the plurality of epilepsy patients (I patients) is set as a value of a general-purpose management limit L, and the management limit adjusting process 62 may be used by a specialist such as a doctor in order to adjust the general-purpose management limit L to a value corresponding to the patient j.

The data forming the epileptic seizure prediction model 73 of the patient i is transferred from the constructing device 51 to the predicting device 1 having the patient i as a subject, and is stored as data forming the epileptic seizure prediction model 22 of the patient (subject) i, into the storage device 20 of the predicting device 1 (see FIG. 3). The data forming the model 73 is transferred to the predicting device 1, for example, when, in order to newly obtain or update the epileptic seizure predicting computer program 21, data forming the model 22 is downloaded as a part of the program 21 by a computer implementing the predicting device 1. The processing unit 10 of the predicting device 1 can read out, from the storage device 20, the data forming the epileptic seizure prediction model 22, and can cause the epileptic seizure prediction model 22 to function. Among pieces of data forming the epileptic seizure prediction model 73 of the patient i, data that is transferred to the predicting device 1 includes the management limit L but may not necessarily include the data forming an autoencoder AE. In this case, the data forming the autoencoder AE may be held by the constructing device 51 or an external device such as a server computer that provides a service for epilepsy prediction.

The processing unit 10 of the predicting device 1 can execute the management limit adjusting process 13 with respect to the epileptic seizure prediction model 22 set in the storage device 20 (see FIG. 3). For example, the management limit adjusting process 13 is a process that allows a user or a specialist such as a doctor to refer to a management limit L set in the storage device 20 and perform an operation of adjusting the set management limit (default value) L.

The management limit adjusting process 13 in the predicting device 1 may also be used by a specialist such as a doctor in order to adjust a general-purpose management limit L set in the storage device 20 to a value corresponding to the patient j.

Figure 8:
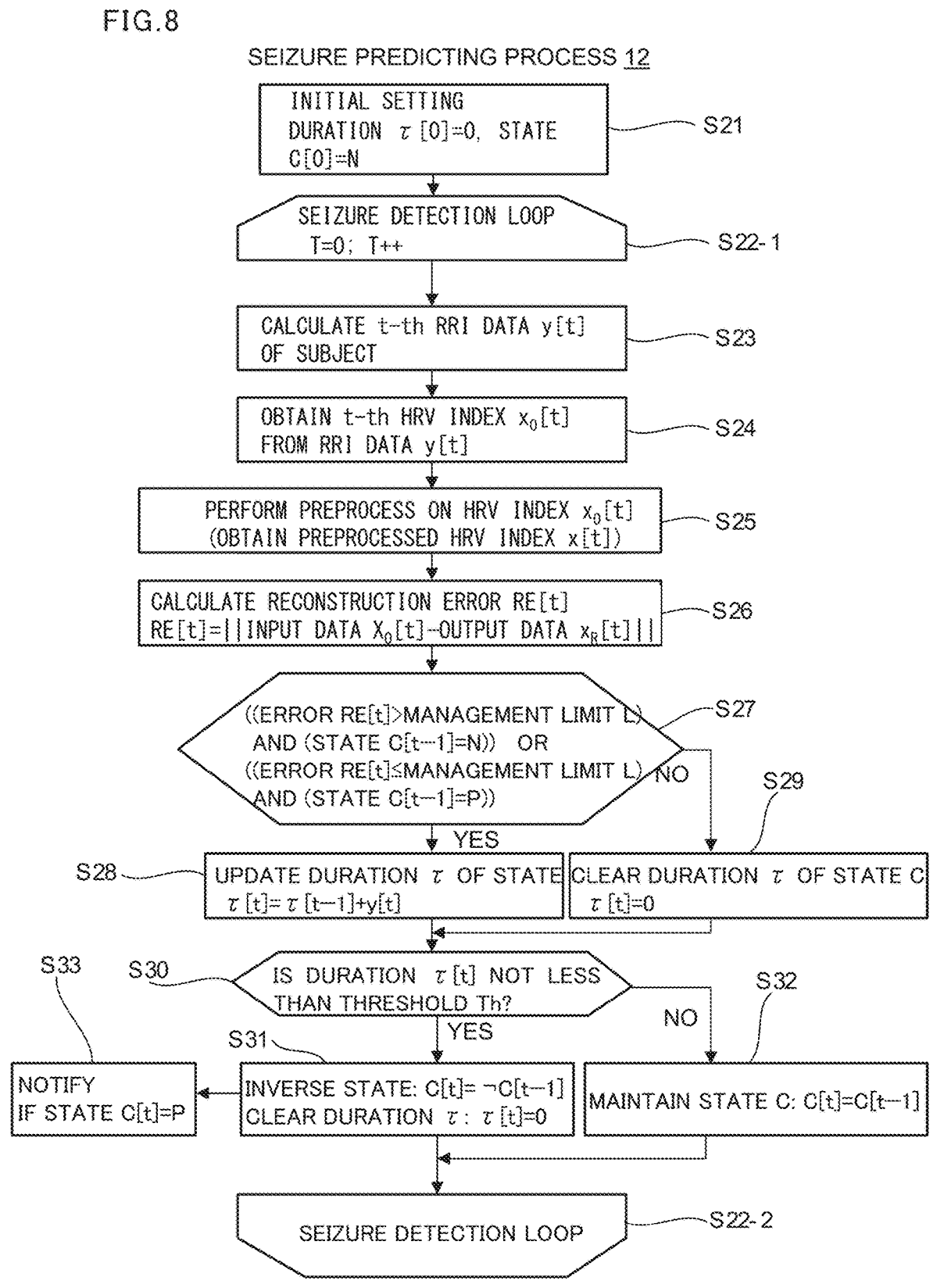

FIG. 8 shows a seizure predicting process 12 performed by the predicting device 1 having the epileptic seizure prediction model 22 installed therein. In the seizure predicting process 12, after initial setting is performed in step S21, a seizure detection loop (from step S22-1 to step S22-2) is repeatedly executed.

In the initial setting, a duration $\tau[0]$ is set to zero, and a state C[0] is set to N. The duration $\tau$ is a variable indicating a duration of a state where the reconstruction error RE(t) exceeds the management limit L or a state where the reconstruction error RE(t) does not exceed the management limit L. The state C takes a value of P or N, where P represents Positive (peri-ictal period) and N represents Negative (seizure-free interval). During execution of the seizure detection loop, the predicting device 1 receives R wave data from the heart rate measuring instrument 2 and stores the R wave data into the storage device 20. In the seizure predicting process 12, seizure prediction is performed on the basis of the received R wave data. In the seizure detection loop, t is a count value, where the initial value thereof is zero and the count value is incremented every time the loop is repeated.

In the seizure detection loop, first, the t-th RRI data y[t] of the subject (the user of the predicting device 1) is calculated from the received R wave data (step S23). Subsequently, the t-th HRV index $x_0[t]$ is obtained from the RRI data y[t] (step S24). Similar to the model construction, the HRV index $x_0[t]$ is composed of eight HRV indexes (meanNN, SDNN, RMSSD, NN50, Total Power, LF/HF, LFnu, HFnu), and serves as input data to the autoencoder AE.

Further, preprocessing is performed on the HRV index $x_0[t]$, to obtain a preprocessed HRV index x[t] (step S25). The preprocessing is a process similar to the standardization in step S13 shown in FIG. 6.

The preprocessed HRV index x[t] is provided, as input data, to the input layer of the autoencoder AE forming the epileptic seizure prediction model 22. Reconstruction data of x[t] is outputted as output data from the output layer of the autoencoder AE. Similar to the input data, the output data is composed of eight HRV indexes (meanNN, SDNN, RMSSD, NN50, Total Power, LF/HF, LFnu, HFnu). The output data is subjected to post-processing, and post-processed output data $x_R[t]$ is obtained.

Then, a reconstruction error REM is calculated from the input data $x_0[t]$ and the output data $x_R[t]$ (step S26). In the embodiment, the reconstruction error RE[t] is calculated as an L1 norm of a vector (reconstruction error of meanNN, reconstruction error of SDNN, reconstruction error of RMSSD, reconstruction error of NN50, reconstruction error of Total Power, reconstruction error of LF/HF, reconstruction error of LFnu, reconstruction error of HFnu) indicating the difference between the input data x0[t] and the output data $x_R[t]$.

In the subsequent steps S27, S28, S29, S30, S31, and S32, a detection process of detecting a peri-ictal period is performed on the basis of the reconstruction error RE. In this detection process, when the reconstruction error RE continuously exceeds the management limit L for Th[s](YES in step S30), P (peri-ictal period) is determined. That is, a sign of an epileptic seizure is detected. Meanwhile, when the reconstruction error RE is continuously lower than the management limit L for Th[s](NO in step S30), N (seizure-free interval) is determined. Here, Th is set to 10 seconds.

In the embodiment, even when the reconstruction error RE momentarily becomes higher or lower than the management limit L, the state C is not immediately changed. Instead, when a state where the reconstruction error RE is higher or lower than the management limit L continues for Th[s], the state C is changed (inversed: step S31). Therefore, an erroneous detection due to momentary fluctuation of the reconstruction error RE can be prevented. In the present embodiment, 99% of the reconstruction error RE in a seizure-free interval is normal, but in the remainder of 1%, the reconstruction error RE may exceed the management limit L even in a seizure-free interval. However, as described above, for detection of a peri-ictal period, it is necessary for the reconstruction error RE to continuously exceed the management limit L for a predetermined time. Therefore, even when a reconstruction error RE corresponding to the above-mentioned 1% occurs, an erroneous detection of a peri-ictal period is prevented.

In the seizure detection loop, when the state C corresponds to P (peri-ictal period), a notification process that notifies that the subject is in a peri-ictal period (step S33) is performed. For the notification, various forms such as sound, character indication, light, and the like can be adopted. The notification may be performed by the device itself that has executed the seizure predicting process 12, or may be performed by, for example, a device different from the device that has executed the predicting process 12. For example, the seizure predicting process 12 may be executed by a smartphone of the subject P, and the notification may be performed by a wearable terminal such as a smartwatch of the subject P.

In the present embodiment, during the model construction, learning by the autoencoder AE and setting of the management limit L are performed by using HRV index data generated from an electrocardiographic signal of a subject, who is the user of the predicting device 1. However, during the model construction, it is not necessary to use HRV index data generated from an electrocardiographic signal of a subject who is the user of the predicting device 1.

For example, in a stage before a subject who is a new user of the predicting device 1 starts using the predicting device 1 (such as when the predicting device 1 or the seizure predicting computer program 21 is purchased), it is in actuality difficult to construct a model using HRV index data generated from an electrocardiographic signal of the subject. Thus, for example, at the time point when the subject starts using the predicting device 1, the predicting device 1 has stored therein a model 22 generated from data of a plurality of other epilepsy patients, and the subject can start using the predicting device 1 in that state. Then, while the predicting device 1 is used, an electrocardiographic signal (or R wave data) of the subject is transmitted to the model constructing device 51 via a network. The model constructing device 51 executes the model constructing process 61 from HRV index data (HRV index data in a seizure-free interval) of a plurality of epilepsy patients to which the subject has been added. Data forming a generated new epileptic seizure prediction model 73 is transmitted to the predicting device 1 via a network. The predicting device 1 stores the data forming the new epileptic seizure prediction model, into the storage device 20, and can use the data in the epileptic seizure predicting process 12.

With this configuration, the epileptic seizure prediction model can be updated in accordance with increase in the number of the users of the predicting device 1. The data forming the new epileptic seizure prediction model 73 may be transmitted for update to a predicting device 1 of another subject.

Figure 9A:
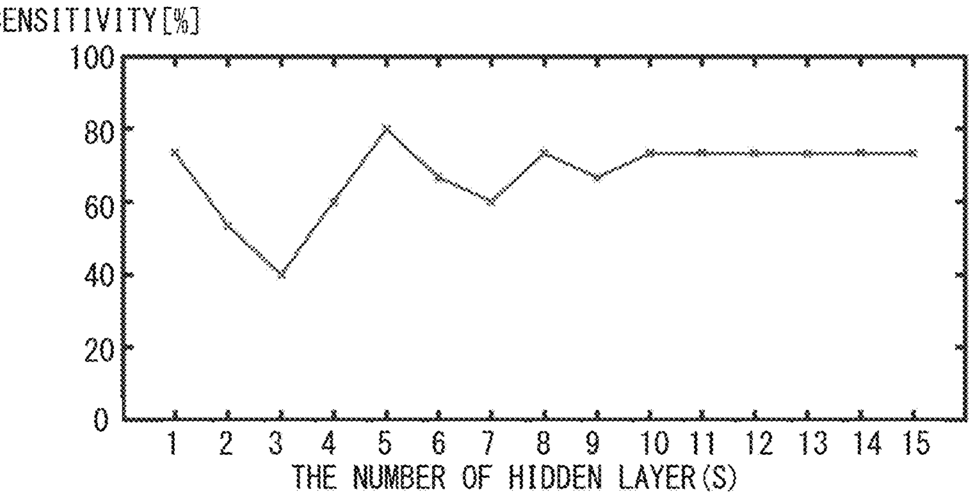
FIG. 9 shows experimental results of seizure prediction.
Figure 9B:
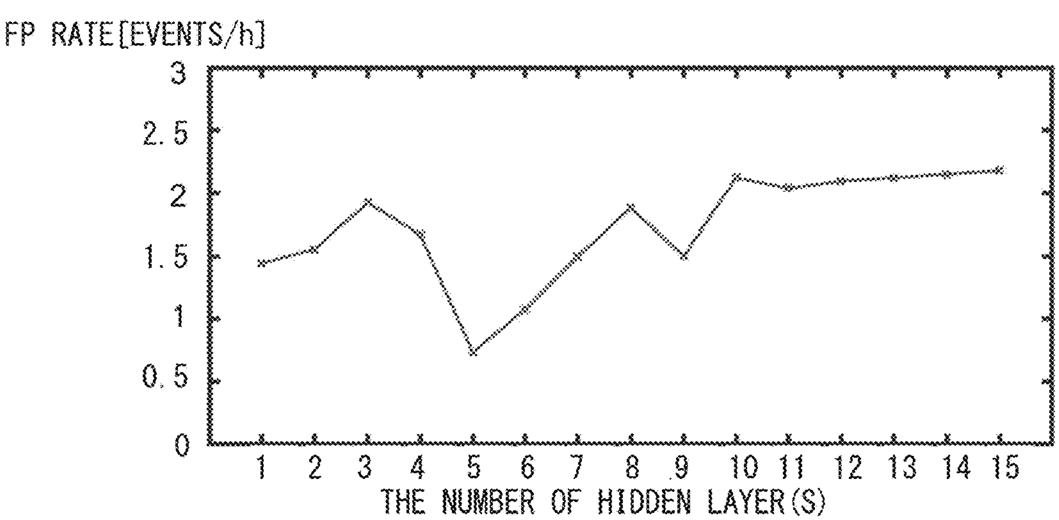
Figure 9C:
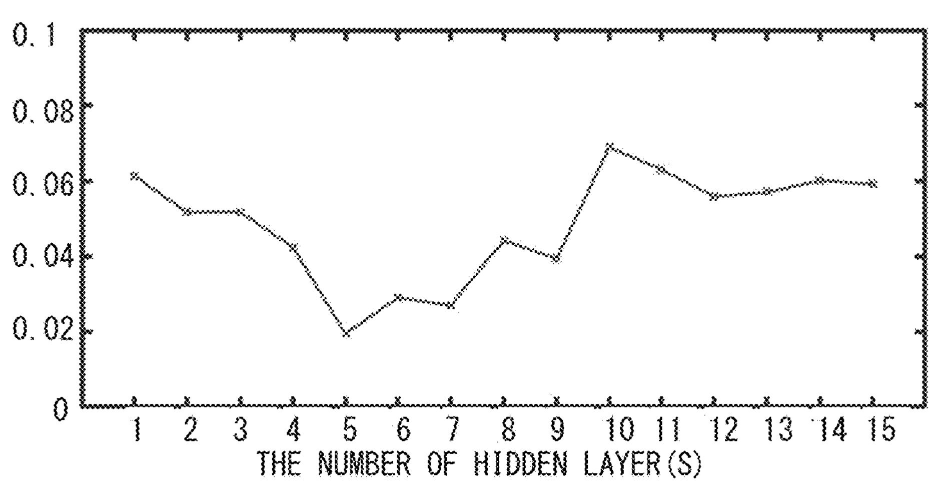

FIG. 9A, FIG. 9B, and FIG. 9C show experimental results of seizure predictions using the predicting device 1 of the embodiment. In the experiment, a logistic sigmoid function was used as a transfer function for the encoder. FIG. 9A shows an experimental result regarding sensitivity. In FIG. 9A, the horizontal axis represents the number of units of the hidden layer, and the vertical axis shows sensitivity. As shown in FIG. 9A, the predicting device 1 has generally good sensitivity. In particular, when the number of units of the hidden layer is 5, a good result of about 80% is obtained.

FIG. 9B shows an experimental result regarding False Positive rate. In FIG. 9B, the horizontal axis represents the number of units of the hidden layer, and the vertical axis represents False Positive rate. The False Positive rate indicates the number of times (the number of times per hour) of erroneous detections, i.e., the number of times a peri-ictal period was erroneously detected in a seizure-free interval. As shown in FIG. 9B, the False Positive rate is generally low. In particular, when the number of units of the hidden layer is 5, a good result of about 0.7 is obtained.

FIG. 9C shows an experimental result regarding the proportion (proportion of duration under false alarms) of time that was erroneously detected as a peri-ictal period, in a verification seizure-free interval. In FIG. 9C, the horizontal axis represents the number of units of the hidden layer, and the vertical axis represents the proportion (proportion of duration under false alarms) of time that was erroneously detected as a peri-ictal period, in the verification seizure-free interval. As shown in FIG. 9, the proportion of the time erroneously detected as a peri-ictal period in the verification seizure-free interval is generally low. In particular, when the number of units of the hidden layer is 5, a good result of about 0.02% is obtained.

3. Additional Note

The present invention is not limited to the above-described embodiment, and various modifications thereof can be made.

REFERENCE SIGNS LIST

1 epileptic seizure predicting device
2 heart rate measuring instrument
10 processing unit
12 seizure predicting process
13 management limit adjusting process
20 storage device
21 computer program
21A electrode
22 epileptic seizure prediction model
30 communication unit
51 epileptic seizure prediction model constructing device
60 processing unit
61 model constructing process
62 management limit adjusting process
70 storage device
71 computer program
72 HRV index data
73 epileptic seizure prediction model
100 system

The invention claimed is:

1. An epileptic seizure predicting device configured to execute a seizure predicting process, the seizure predicting process comprising:

a process of providing, as input data, electrocardiographic index data generated from an electrocardiographic signal of a subject, to an autoencoder that has been provided with and has learned with, as learning input data, learning electrocardiographic index data generated from an electrocardiographic signal of an epilepsy patient, and obtaining output data which is reconstruction data of the input data;

a process of calculating a reconstruction error calculated from an error between the input data and the output data of the subject; and a detection process of detecting a sign of an epileptic seizure of the subject on the basis of whether the reconstruction error exceeds a management limit, wherein detection that the reconstruction error is equal to or lower than the management limit indicates that the subject is in a seizure-free interval of epilepsy, wherein the electrocardiographic index data includes a plurality of types of heart rate variability (HRV) indexes comprising meanNN, SDNN, RMSSD, NN50, Total Power, LF/HF, LFnu, and HFnu, wherein the reconstruction error is a single error calculated as an L1 norm of a vector composed of a reconstruction error of meanNN, a reconstruction error of SDNN, a reconstruction error of RMSSD, a reconstruction error of NN50, a reconstruction error of Total Power, a reconstruction error of LF/HF, a reconstruction error of LFnu, and a reconstruction error of HFnu.

2. The epileptic seizure predicting device according to claim 1, wherein the learning electrocardiographic index data is generated from an electrocardiographic signal in a seizure-free interval of the epilepsy patient.

3. The epileptic seizure predicting device according to claim 1, wherein in the detection process, the sign of the epileptic seizure of the subject is detected when the error continuously exceeds the management limit for a predetermined time.

4. The epileptic seizure predicting device according to claim 1, wherein the electrocardiographic index data is calculated on the basis of an RRI (R-R Interval) generated from the electrocardiographic signal of the subject.

5. The epileptic seizure predicting device according to claim 1, wherein the learning electrocardiographic index data is generated from electrocardiographic signals of a plurality of epilepsy patients, and the plurality of epilepsy patients include the subject and an epilepsy patient other than the subject.

6. The epileptic seizure predicting device according to claim 1, wherein the epileptic seizure predicting device is configured to further execute an adjusting process for adjusting the management limit stored in advance in a storage device.

7. A method to be performed by a computer in order to analyze electrocardiographic index data generated from an electrocardiographic signal of a subject, the method comprising the steps, performed by the computer, of:

providing, as input data, electrocardiographic index data generated from an electrocardiographic signal of the subject, to an autoencoder that has been provided with and has learned with, as learning input data, learning electrocardiographic index data generated from an electrocardiographic signal of an epilepsy patient, and obtaining output data which is reconstruction data of the input data;

calculating a reconstruction error calculated from an error between the input data and the output data of the subject; and determining whether the reconstruction error exceeds a management limit, wherein detection that the reconstruction error is equal to or lower than the management limit indicates that the subject is in a seizure-free interval of epilepsy, wherein the electrocardiographic index data includes a plurality of types of heart rate variability (HRV) indexes comprising meanNN, SDNN, RMSSD, NN50, Total Power, LF/HF, LFnu, and HFnu, wherein the reconstruction error is a single error calculated as an L1 norm of a vector composed of a reconstruction error of meanNN, a reconstruction error of SDNN, a reconstruction error of RMSSD, a reconstruction error of NN50, a reconstruction error of Total Power, a reconstruction error of LF/HF, a reconstruction error of LFnu, and a reconstruction error of HFnu.

8. A non-transitory computer-readable storage medium with a seizure predicting computer program stored thereon, wherein the program is configured to cause a computer to execute a seizure predicting process, the seizure predicting process comprising:

a process of providing, as input data, electrocardiographic index data generated from an electrocardiographic signal of a subject, to an autoencoder that has been provided with and has learned with, as learning input data, learning electrocardiographic index data generated from an electrocardiographic signal of an epilepsy patient, and obtaining output data which is reconstruction data of the input data;

a process of calculating a reconstruction error calculated from an error between the input data and the output data of the subject; and a detection process of detecting a sign of an epileptic seizure of the subject on the basis of whether the reconstruction error exceeds a management limit, wherein detection that the reconstruction error is equal to or lower than the management limit indicates that the subject is in a seizure-free interval of epilepsy, wherein the electrocardiographic index data includes a plurality of types of heart rate variability (HRV) indexes comprising meanNN, SDNN, RMSSD, NN50, Total Power, LF/HF, LFnu, and HFnu, wherein the reconstruction error is a single error calculated as an L1 norm of a vector composed of a reconstruction error of meanNN, a reconstruction error of SDNN, a reconstruction error of RMSSD, a reconstruction error of NN50, a reconstruction error of Total Power, a reconstruction error of LF/HF, a reconstruction error of LFnu, and a reconstruction error of HFnu.

9. A model constructing device configured to execute a model constructing process for epileptic seizure prediction, the model constructing process comprising:

a process of providing, as input data, electrocardiographic index data generated from an electrocardiographic signal of a subject, to an autoencoder that has been provided with and has learned with, as learning input data, learning electrocardiographic index data generated from an electrocardiographic signal of an epilepsy patient, and obtaining output data which is reconstruction data of the input data;

a calculation process of calculating a reconstruction error calculated from an error between the input data and the output data; and a setting process of setting, on the basis of the reconstruction error, a management limit, wherein detection that the reconstruction error is equal to or lower than the management limit indicates that the subject is in a seizure-free interval of epilepsy, wherein the electrocardiographic index data includes a plurality of types of heart rate variability (HRV) indexes comprising meanNN, SDNN, RMSSD, NN50, Total Power, LF/HF, LFnu, and HFnu, wherein the reconstruction error is a single error calculated as an L1 norm of a vector composed of a reconstruction error of meanNN, a reconstruction error of SDNN, a reconstruction error of RMSSD, a reconstruction error of NN50, a reconstruction error of Total Power, a reconstruction error of LF/HF, a reconstruction error of LFnu, and a reconstruction error of HFnu.

10. The model constructing device according to claim 9, wherein in the setting process, the management limit is set such that: a predetermined proportion of errors that accounts for a majority of a plurality of the errors calculated in the calculation process does not exceed the management limit; and a remainder of the plurality of the errors exceeds the management limit.

11. The model constructing device according to claim 10, wherein the predetermined proportion that accounts for the majority is a proportion in a range of not less than 90% and less than 100%.

12. A method for constructing a model for epileptic seizure prediction, the method comprising:

providing, as input data, electrocardiographic index data generated from an electrocardiographic signal of a subject, to an autoencoder that has been provided with and has learned with, as learning input data, learning electrocardiographic index data generated from an electrocardiographic signal of an epilepsy patient, and obtaining output data which is reconstruction data of the input data;

calculating a reconstruction error calculated from an error between the input data and the output data; and setting, on the basis of the reconstruction error, a management limit, wherein detection that the reconstruction error is equal to or lower than the management limit indicates that the subject is in a seizure-free interval of epilepsy, wherein the electrocardiographic index data includes a plurality of types of heart rate variability (HRV) indexes comprising meanNN, SDNN, RMSSD, NN50, Total Power, LF/HF, LFnu, and HFnu, wherein the reconstruction error is a single error calculated as an L1 norm of a vector composed of a reconstruction error of meanNN, a reconstruction error of SDNN, a reconstruction error of RMSSD, a reconstruction error of NN50, a reconstruction error of Total Power, a reconstruction error of LF/HF, a reconstruction error of LFnu, and a reconstruction error of HFnu.

13. A non-transitory computer-readable storage medium with a model constructing computer program stored thereon, wherein the program configured to cause a computer to execute a model constructing process, the model constructing process comprising:

a process of providing, as input data, electrocardiographic index data generated from an electrocardiographic signal of a subject, to an autoencoder that has been provided with and has learned with, as learning input data, learning electrocardiographic index data generated from an electrocardiographic signal of an epilepsy patient, and obtaining output data which is reconstruction data of the input data;

a calculation process of calculating a reconstruction error calculated from an error between the input data and the output data; and a setting process of setting, on the basis of the reconstruction error, a management limit, wherein detection that the reconstruction error is equal to or lower than the management limit indicates that the subject is in a seizure-free interval of epilepsy, wherein the electrocardiographic index data includes a plurality of types of heart rate variability (HRV) indexes comprising meanNN, SDNN, RMSSD, NN50, Total Power, LF/HF, LFnu, and HFnu, wherein the reconstruction error is a single error calculated as an L1 norm of a vector composed of a reconstruction error of meanNN, a reconstruction error of SDNN, a reconstruction error of RMSSD, a reconstruction error of NN50, a reconstruction error of Total Power, a reconstruction error of LF/HF, a reconstruction error of LFnu, and a reconstruction error of HFnu.

* * * * *